United States Patent
Makam et al.

(10) Patent No.: US 9,605,289 B2
(45) Date of Patent: Mar. 28, 2017

(54) PROCESS OF PRODUCTION AND EXTRA-CELLULAR SECRETION OF LIPIDS

(71) Applicant: Roshan Viswanath Makam, Bangalore (IN)

(72) Inventors: Roshan Viswanath Makam, Bangalore (IN); Krishnamurthy Venkatappa, Bangalore (IN)

(73) Assignee: ROSHAN VISWANATH MAKAM, Bangalore (IN)

( * ) Notice: Subject to any disclaimer, the term of this patent is extended or adjusted under 35 U.S.C. 154(b) by 0 days.

(21) Appl. No.: 14/763,037

(22) PCT Filed: Nov. 10, 2014

(86) PCT No.: PCT/IB2014/002386
§ 371 (c)(1),
(2) Date: Jul. 23, 2015

(87) PCT Pub. No.: WO2015/071726
PCT Pub. Date: May 21, 2015

(65) Prior Publication Data
US 2016/0265011 A1    Sep. 15, 2016

(30) Foreign Application Priority Data

Nov. 12, 2013  (IN) ............................ 5134/CHE/2013

(51) Int. Cl.
*C12P 1/00* (2006.01)
*C12P 7/64* (2006.01)
*C12N 1/12* (2006.01)

(52) U.S. Cl.
CPC .............. *C12P 7/6463* (2013.01); *C12N 1/12* (2013.01)

(58) Field of Classification Search
None
See application file for complete search history.

(56) References Cited

FOREIGN PATENT DOCUMENTS

WO    2010/009348 A2    1/2010
WO    2010/132413 A1    11/2010

OTHER PUBLICATIONS

Kropat et al., The Plant Journal, 2011, vol. 66, p. 770-780.*
Endo et al., Agr. Biol. Chem., 1974, vol. 38, No. 1, p. 9-18.*
Cheirsilp et al., online Feb. 2012, Bioresource Technology, 2012, vol. 110, p. 510-516.*
Kind et al, "Qualitative analysis of algal secretions with multiple mass spectrometric platforms", J Chromatogr A., vol. 1244, Jun. 29, 2012, pp. 139-147.
Liu et al., "Effect of iron on growth and lipid accumulation in Chlorella vulgaris", Bioresource Technology, vol. 99, No. 11, Jul. 1, 2008, pp. 4717-4722.
Mandalam et al., "Elemental balancing of biomass and medium composition enhances growth capacity in high-density Chlorella vulgaris cultures", Biotechnology and Bioengineering, vol. 59, No. 5, Sep. 5, 1998, pp. 605-611.
Sharma et al., "High lipid induction in microalgae for biodiesel production", Energies, vol. 5, May 18, 2012, pp. 1532-1553.
Urzica et al., "Remodeling of Membrane Lipids in Iron-starved Chlamydomonas", Journal of Biological Chemistry, vol. 288, No. 42, Oct. 18, 2013, pp. 1-24.
Yeesang et al., "Effect of nitrogen, salt, and iron content in the growth medium and light intensity on lipid production by microalgae isolated from freshwater sources in Thailand", Bioresource Technology, vol. 102, No. 3, Feb. 1, 2011, pp. 3034-3040.

* cited by examiner

*Primary Examiner* — Kade Ariani
(74) *Attorney, Agent, or Firm* — Seed IP Law Group LLP

(57) ABSTRACT

The present disclosure relates to a process of production and extra-cellular secretion of lipids from an oleaginous microorganism by using a modified growth medium deficient in nitrogen and iron.

7 Claims, 3 Drawing Sheets

PROCESS OF PRODUCTION AND EXTRA-CELLULAR SECRETION OF LIPIDS

FIELD OF INVENTION

The present disclosure relates to a process of production and extra-cellular secretion of lipids from a microorganism.

BACKGROUND OF THE INVENTION

Biodiesel obtained from alternate renewable resources has received considerable attention for dealing with the deteriorating situation of world energy supply. Biosynthesis of lipids by microorganisms such as bacteria, yeasts and algae is well established. There are many commercial applications of lipids in the area of food industry, pharmaceuticals, and cosmetics. Lipids such as triglycerides, serve as precursors for biodiesel. Triglycerides, once extracted, can be converted into biodiesel through trans-esterification reactions. Many species of oleaginous microorganisms have been reported to accumulate significant amounts of lipids (Meng et al., *Renewable Energy*, 2009, 34, 1-5).

Microalgae are a highly specialized group of oleaginous microorganisms adapted to various ecological habitats. Under stress and adverse environmental conditions, many species of microalgae alter their lipid biosynthetic pathways favoring the formation and accumulation of triglycerides (20-50% dry cell weight). After being synthesized, triglycerides are deposited in to densely packed cytosolic lipid bodies. (Hu et al., *The Plant Journal*, 2008, 54, 621-639). Triglycerides generally serve as energy storage molecules in microalgae.

Significant amount of research has been carried out to identify and develop efficient lipid induction techniques in microalgae by modulating various environmental factors such as nutrient availability, osmotic pressure, radiation exposure, pH, temperature, exposure to heavy metals and other chemicals (Sharma el al., *Energies*, 2012, 5, 1532-1553).

WO1989000606 describes the production of omega-3 (n–3) lipids in microalgae cells subjected to limiting quantities of nitrogen and phosphorous in the medium.

WO2001054510 describes enhanced production of microbial lipids in eukaryotic microorganisms grown in a non-alcohol carbon source and a limiting nutrient source.

U.S. Pat. No. 8,475,543 describes a process of production of bio-fuels from algae including cultivating oil-producing algae by promoting sequential photoautotrophic and heterotrophic growth. The heterotrophic growth stage is initiated using a stress induction mechanism including at least one of light deprivation, nutrient deprivation, injection of a reactive oxygen source, a lipid trigger, and chemical additives. Further, the process describes extracting the oil from the oil-producing algae by lysis of the cells.

Production of biodiesel from microalgae is an emerging field and appears to be a potential alternative bio-resource. However, current technology involves intra-cellular production of triglycerides or lipids in the microalgae, thus creating a roadblock in downstream processing i.e., the microalgae cells have to be harvested, dried and ruptured either by mechanical or biochemical methods for the extraction of lipids, thereby increasing time and cost factors.

In light of current available technology and scientific advances, there exists a need for developing a cost-effective and efficient process that eliminates the need for harvesting and rupturing the microbial cells for extraction of the intra-cellular lipids.

SUMMARY OF THE INVENTION

An aspect of the present disclosure relates to a process of production and extra-cellular secretion of lipids.

An aspect of the present disclosure relates to a process of enhanced production and extra-cellular secretion of lipid comprising of: (a) obtaining a biomass of an oleaginous microorganism; and (b) culturing the biomass of an oleaginous microorganism in a modified growth medium deficient in nitrogen and iron, resulting in enhanced production and extra-cellular secretion of lipids.

This summary is provided to introduce concepts related to a process of synthesis, and extra-cellular secretion of lipids by using a modified growth medium deficient in nitrogen and iron. This summary is not intended to identify essential features of the claimed subject matter nor is it intended for use in determining or limiting the scope of the claimed subject matter.

BRIEF DESCRIPTION OF ACCOMPANYING DRAWINGS

The following drawings form part of the present specification and are included to further illustrate aspects of the present disclosure. The disclosure may be better understood by reference to the drawings in combination with the detailed description of the specific embodiments presented herein.

DETAILED DESCRIPTION OF THE INVENTION

Figure 1:
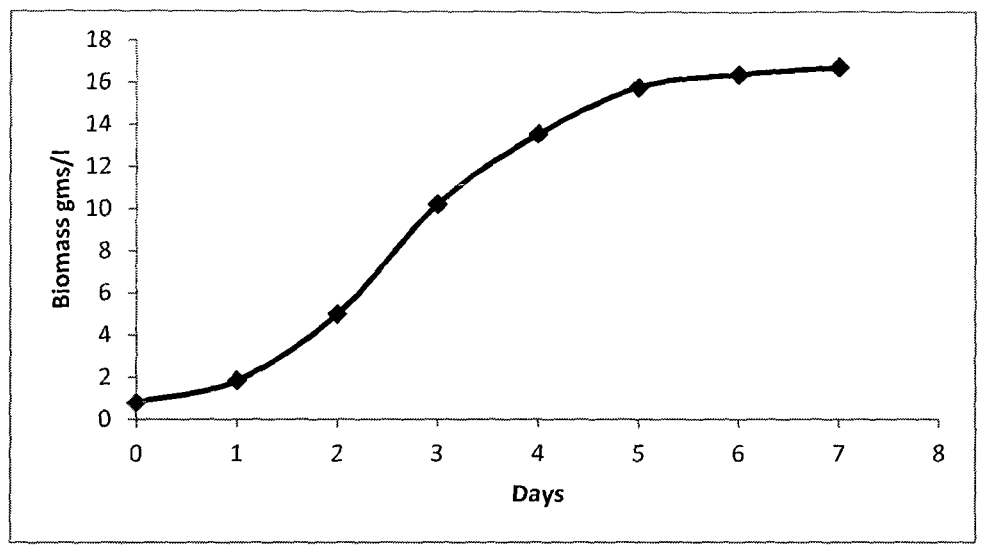
FIG. 1 shows a graphical representation of biomass growth measured in grams/liter (g/L) in various media, in accordance with an embodiment of the present disclosure.

Those skilled in the art will be aware that the disclosure described herein is subject to variations and modifications other than those specifically described. It is to be understood that the disclosure described herein includes all such variations and modifications. The disclosure also includes all such steps, features, compositions and compounds referred to or indicated in this specification, individually or collectively, and any and all combinations of any or more of the steps or features.

Definitions

For convenience, before further description of the present disclosure, certain terms employed in the specification and examples are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a", "an" and "the" are used to refer to one or to more than one (i.e., to at least one) of the grammatical object of the article.

The term "plurality" means more than one.

The terms "at least two," "more than one" and "plurality" are used interchangeably.

Throughout this specification, unless the context requires otherwise the word "comprise", and variations such as "comprises" and "comprising", will be understood to imply the inclusion of a stated element or step or group of element or steps but not the exclusion of any other element or step or group of element or steps.

The term "including" is used to mean "including but not limited to". "Including" and "including but not limited to" are used interchangeably.

The terms "microorganism" and "microbe" are used interchangeably to mean microscopic unicellular organism.

The term "microbial biomass" means material produced by growth and propagation of microbial cells. Microbial biomass may contain cells and/or intracellular contents and extracellular compounds secreted by the cells.

The term "microbial culture" or "culture" means microorganisms multiplied and reproduced in a pre-determined growth medium under controlled laboratory conditions.

The term "growth medium" or "culture medium" means a solid or liquid preparation containing all the nutrients required for the growth of a specific microorganism.

The term "sub-culturing" means transferring microbial cells from a previous microbial culture to a fresh growth medium to obtain a sub-culture. It prolongs the life and increases the number of microbial cells in a culture.

The term "sub-culture" means a new microbial culture obtained by transferring microbial cells from a previous culture to a fresh growth medium.

The term "oleaginous microorganism" means a microbe with a lipid content of at least 20-25%.

The term "algae" means eukaryotic microorganisms that have chlorophyll a and are photoautotrophic.

The term "microalgae" means eukaryotic photoautotrophic microorganisms that produce macromolecules such as lipids.

The term "lipids" means a class of hydrocarbons that are soluble in non-polar solvents and are relatively insoluble in water. Lipid molecules consist of long hydrocarbon tails which are hydrophobic in nature. Examples of lipids include fatty acids, monoglycerides, diglycerides, triglycerides etc.

The terms "triacylglyceride", "triglyceride" and "TAG" are used interchangeably to mean an ester derived from glycerol and three fatty acids.

In an embodiment of the present disclosure, there is provided a process of production and extra-cellular secretion of lipids.

In an embodiment of the present disclosure, the lipids are TAGs.

In an embodiment of the present disclosure, there is provided a process of production of TAGs in an oleaginous microorganism by using a modified growth medium deficient in nitrogen.

In an embodiment of the present disclosure, there is provided a process of production of TAGs in an oleaginous microorganism by using a modified growth medium deficient in iron.

In a preferred embodiment of the present disclosure, there is provided a process of production of TAGs in an oleaginous microorganism by using a modified growth medium deficient in iron and nitrogen.

In an embodiment of the present disclosure, there is provided a process of extra-cellular secretion of TAGs from an oleaginous microorganism by using a modified growth medium deficient in iron.

In a preferred embodiment of the present disclosure, there is provided a process of production and extra-cellular secretion of TAGs from an oleaginous microorganism by using a modified growth medium deficient in nitrogen and iron.

In an embodiment of the present disclosure, there is provided a process of production and extra-cellular secretion of TAGs, said process comprising: (a) growing a culture of an oleaginous microorganism in an unmodified growth-medium for 5-7 days; (b) isolating the microbial biomass by centrifugation; and (c) growing the microbial biomass from (b) in a modified growth-medium deficient in nitrogen and iron.

In an embodiment of the present disclosure, there is provided a process of production and extra-cellular secretion of TAGs, said process comprising: (a) obtaining a biomass of an oleaginous microorganism; and (b) culturing the biomass of an oleaginous microorganism in a modified growth medium deficient in nitrogen and iron, resulting in enhanced production and extra-cellular secretion of lipids.

In an embodiment of the present disclosure, the unmodified growth media is Sanger and Granick medium.

In an embodiment of the present disclosure, the unmodified growth media is TAP medium.

In an embodiment of the present disclosure, the unmodified growth media is Sueoka's high salt medium.

In a preferred embodiment of the present disclosure, the unmodified growth media is nutrient broth growth medium.

In an embodiment of the present disclosure, the pH of the nutrient broth growth media is 7.0.

In an embodiment of the present disclosure, the microbial biomass concentration on day 5 of growth in Sanger and Granick medium is 10.9 mg/L.

In an embodiment of the present disclosure, the microbial biomass concentration on day 5 of growth in Sueoka's high salt medium is 13.2 mg/L.

In an embodiment of the present disclosure, the microbial biomass concentration on day 5 of growth in TAP medium is 12.1 mg/L.

In an embodiment of the present disclosure, the microbial biomass concentration on day 5 of growth in nutrient broth media is 15.8 mg/L.

In an embodiment of the present disclosure, the growth medium deficient in iron has 0.1% yeast extract, 0.1% beef extract, 0.2% tryptose and 1% glucose.

In an embodiment of the present disclosure, the pH of the growth medium deficient in iron is 7.0.

In an embodiment of the present disclosure, the growth medium deficient in nitrogen has 0.1% yeast extract, 0.1% beef extract 0.2% glucose and trace amounts of $FeSO_4$.

In an embodiment of the present disclosure, the pH of the growth medium deficient in nitrogen is 7.0.

In a preferred embodiment of the present disclosure, the modified growth medium deficient in nitrogen and iron has 0.1% yeast extract, 0.1% beef extract and 1% glucose.

In an embodiment of the present disclosure, the pH of the modified growth medium deficient in nitrogen and iron is in the range of 6.5-7.5.

In a preferred embodiment of the present disclosure, the pH of the modified growth medium deficient in nitrogen and iron is 7.0.

In an embodiment of the present disclosure, the oleaginous microorganism is an algae.

In an embodiment of the present disclosure, the alga is a microalgae.

In an embodiment of the present disclosure, the microalga is selected from the group not limited to *Chlamydomonas reinhardtii*, *Chlamydomonas caudate Wille*, *Chlamydomonas moewusii*, *Chlamydomonas nivalis*, and *Chlamydomonas ovoidae*.

In a preferred embodiment of the present disclosure, the microalga is *Chlamydomonas reinhardtii*.

In an embodiment of the present disclosure, the glucose concentration of the unmodified growth medium is in the range of 5 g/L to 24.0 g/L.

In a preferred embodiment of the present disclosure, the glucose concentration of the unmodified growth medium is 23.11 g/L.

In an embodiment of the present disclosure, the microbial culture grown in unmodified growth medium is subjected to a light cycle period ranging from 4.69-hours to 24-hours.

In an embodiment of the present disclosure, the microbial culture grown in unmodified growth medium is subjected to a light cycle period ranging from 8-hours to 16-hours.

In a preferred embodiment of the present disclosure, the microbial culture grown in unmodified growth medium is subjected to a 16-hour light cycle period.

In an embodiment of the present disclosure, the microbial culture is grown in unmodified growth medium having glucose concentration of 23.11 g/L and exposed to 16-hour light cycle.

In an embodiment of the present disclosure, the modified growth medium deficient in iron and nitrogen comprises of (a) yeast extract in the range of 0.05%-0.2%, (b) beef extract in the range of 0.05%-0.2%, and (c) glucose in the range of 0.5%-3%.

In a preferred embodiment of the present disclosure, the modified growth medium deficient in iron and nitrogen comprises of (a) 0.1% yeast extract, (b) 0.1% beef extract, and (c) 1% glucose.

In an embodiment of the present disclosure, the pH of the modified growth medium deficient in iron and nitrogen is in the range of 6.5-7.5.

In a preferred embodiment of the present disclosure, the pH of the modified growth medium deficient in iron and nitrogen is 7.0

In an embodiment of the present disclosure, the glucose concentration of the modified growth medium deficient in nitrogen and iron is in the range of 5 g/L to 30 g/L.

In a preferred embodiment of the present disclosure, the glucose concentration of the modified growth medium deficient in nitrogen and iron is 23.11 g/L.

In an embodiment of the present disclosure, the biomass of an oleaginous microorganism is grown in a modified growth medium deficient in nitrogen and iron subjected to a light cycle period ranging from 4.69-hours to 24-hours.

In an embodiment of the present disclosure, the biomass of an oleaginous microorganism is grown in a modified medium deficient in nitrogen and iron subjected to a light cycle period ranging from 8-hours to 16-hours.

In a preferred embodiment of the present disclosure, the biomass of an oleaginous microorganism is grown in a modified growth medium deficient in nitrogen and iron subjected to a light cycle period of 16 hours.

In an embodiment of the present disclosure, the biomass of an oleaginous microorganism grown in a modified growth medium deficient in nitrogen and iron has glucose concentration of 23.11 g/L and is subjected to a 16-hour light cycle period.

In an embodiment of the present disclosure, the intracellular TAG concentration in a microbial culture grown in a modified growth medium comprising 23.11 g/L glucose, cultured in 16-hours light cycle and deficient in iron is 1000 mg/L.

In an embodiment of the present disclosure, the extracellular TAG concentration in a microbial culture grown in a growth medium comprising 23.11 g/L glucose, cultured in 16-hours light cycle and deficient in iron is 300 mg/L.

In an embodiment of the present disclosure, 25% of the TAGs produced by a microbial culture grown in a growth medium deficient in iron is secreted extra-cellularly.

In an embodiment of the present disclosure, microbial biomass cultured in a modified growth medium deficient in nitrogen induces TAG synthesis.

In an embodiment of the present disclosure, the intracellular TAG concentration in a microbial culture grown in a growth medium comprising 23.11 g/L glucose, cultured in 16-hours light cycle and deficient in nitrogen is 200 mg/L.

In an embodiment of the present disclosure, the intracellular TAG concentration in a microbial culture grown in a modified growth medium comprising 23.11 g/L glucose, cultured in 16-hours light cycle and deficient in nitrogen is 2000 mg/L.

In a preferred embodiment of the present disclosure, microbial biomass cultured in modified growth medium deficient in both iron and nitrogen enhances TAG synthesis.

In a preferred embodiment of the present disclosure, microbial biomass cultured in modified growth medium deficient in iron and nitrogen enhances extra-cellular secretion of TAGs.

In an embodiment of the present disclosure, the intracellular TAG concentration in a microbial culture grown in a modified growth medium comprising 23.11 g/L glucose, cultured in 16-hours light cycle and deficient in both iron and nitrogen is 3000 mg/L.

In an embodiment of the present disclosure, the extracellular TAG concentration in a microbial culture grown in a modified growth medium comprising 23.11 g/L glucose, cultured in 16-hours light cycle and deficient in both iron and nitrogen is 6000 mg/L.

In an embodiment of the present disclosure, 50%-70% of lipids synthesized by a microbial mass grown in a modified growth medium deficient in both iron and nitrogen are secreted extra-cellularly.

In an embodiment of the present disclosure, 66% of lipids synthesized by a microbial mass grown in a modified growth medium deficient in both iron and nitrogen are secreted extra-cellularly.

In an embodiment of the present disclosure, 100% of lipids secreted extra-cellularly by the microbial biomass cultured in a modified growth medium deficient in both iron and nitrogen are TAGs.

In an embodiment of the present disclosure, 100% of lipids secreted extra-cellularly by the microbial biomass cultured in a modified growth medium deficient in iron are TAGs.

Although the subject matter has been described in considerable detail with reference to certain preferred embodiments thereof, other embodiments are possible.

Although the oleaginous microbial biomass characteristics (yield) were tested in four different media types as mentioned herein, a person skilled in art can use any other media to obtain an oleaginous microbial biomass.

Although production, and extra-cellular secretion of TAGs was tested in media as defined herein deficient in iron or nitrogen or both iron and nitrogen, a person skilled in the art can use any other media composition for production, and extra-cellular secretion of TAGs.

In an embodiment of the present disclosure, there is provided a conventional method of purification, and isolation of extra-cellularly secreted TAGs.

A person skilled in the art can employ other conventional methods to purify or isolate extra-cellularly secreted TAGs.

EXAMPLES

The disclosure will now be illustrated with working examples, which is intended to illustrate the working of disclosure and not intended to take restrictively to imply any limitations on the scope of the present disclosure. Unless defined otherwise, all technical and scientific terms used herein have the same meaning as commonly understood to one of ordinary skill in the art to which this disclosure belongs.

Example 1

Microbial Culture and Growth Media

Microbial culture: The culture of *Chlamydomonas reinhardtii* (ATCC-18798) was procured from American Type Culture Collection (ATCC). The primary culture was stored in 35% glycerol at 20° C. for further use.

Growth medium: Four different types of growth media namely, nutrient broth (NB) medium, tris-acetate-phosphate medium (TAP) medium, Sueoka's high salt medium and Sanger and Granick medium were prepared and used for testing the growth potential of *Chlamydomonas reinhardtii*. The growth media were prepared in distilled water and pH balanced. The media was autoclaved under standard conditions before use.

Nutrient broth growth medium constituents are provided in Table 1.

TABLE 1

| Ingredient | Amount |
| --- | --- |
| Yeast extract | 1 g |
| Beef extract | 1 g |
| Glucose | 10 g |
| Tryptose | 2 g |
| $FeSO_4$ | Trace amounts |
| Distilled water | 1000 mL |
| pH | 7.0 |

TAP growth medium constituents are provided in Table 2.

TABLE 2

| Ingredient | Amount |
| --- | --- |
| TAP salts | |
| $NH_4Cl$ | 15 g |
| $MgSO_4 \cdot 7H_2O$ | 4 g |
| $CaCl_2 \cdot 2H_2O$ | 2 g |
| Distilled water | 1000 mL |
| Phosphate solution | |
| $K_2HPO_4$ | 28.8 g |
| $KH_2PO_4$ | 14.4 g |
| Distilled water | 100 mL |

TABLE 2-continued

| Hutner's trace elements | | |
| --- | --- | --- |
| Ingredient | Amount | Water |
| EDTA disodium salt | 50 g | 250 mL |
| $ZnSO_4 \cdot 7H_2O$ | 22 g | 100 mL |
| $H_3BO_3$ | 11.4 g | 200 mL |
| $MnCl_2 \cdot 4H_2O$ | 5.06 g | 50 mL |
| $CoCl_2 \cdot 6H_2O$ | 1.61 g | 50 mL |
| $CuSO_4 \cdot 5H_2O$ | 1.57 g | 50 mL |
| $(NH_4)_6Mo_7O_{24} \cdot 4H_2O$ | 1.1 g | 50 mL |
| $FeSO_4 \cdot 7H_2O$ | 4.99 g | 50 mL |

All the trace elements except EDTA were mixed by boiling following which EDTA was added to the solution. The solution was cooled to 70° C. and 85 mL hot 20% KOH solution was added. Final volume was adjusted to 1000 mL and allowed to stand for 2 weeks. Subsequently, the solution was filtered through Whatman's filter paper until the solution was clear. Aliquots were made and stored in 4° C. for further use.

TAP medium preparation: 2.42 g of Tris was added to 25 mL solution of TAP salts, 0.375 mL of phosphate solution, 1 mL of Hutner's trace elements and 1 mL of glacial acetic acid. The final volume was adjusted to 1000 mL.

Sueoka's high salt medium constituents are provided in Table 3.

TABLE 3

| Ingredient | Amount |
| --- | --- |
| Beijerinck's solution | |
| $NH_4Cl$ | 100 g |
| $MgSO_4 \cdot 7H2O$ | 4 g |
| $CaCl_2 \cdot 2H2O$ | 2 g |
| Distilled water | 1000 mL |
| Phosphate solution | |
| $K_2HPO_4$ | 288 g |
| $KH_2PO_4$ | 144 g |
| Distilled water | 1000 mL |

Sueoka's high salt medium preparation: 5 mL of Beijerinck's solution was added to 5 mL of phosphate solution and 1 mL of Hutner's trace elements. Final volume was adjusted to 1000 mL.

Sanger and Granick medium constituents are provided in Table 4.

TABLE 4

| Ingredient | Amount |
| --- | --- |
| Trace elements | |
| $H_3BO_3$ | 1 g |
| $ZnSO_4 \cdot 7H_2O$ | 1 g |
| $MnSO_4 \cdot 4H_2O$ | 0.3 g |
| $CoCl_2 \cdot 6H_2O$ | 0.2 g |
| $Na_2MoO_4 \cdot 2H_2O$ | 0.2 g |
| $CuSO_4$ | 0.04 g |
| Distilled water | 1000 mL |
| Sodium citrate solution | |
| Na citrate | 500 g |
| Distilled water | 1000 mL |
| Ferric chloride | |
| $FeCl_3 \cdot 6H_2O$ | 10 g |
| Distilled water | 1000 mL |

TABLE 4-continued

| Ingredient | Amount |
| --- | --- |
| Calcium chloride | |
| $CaCl_2 \cdot 2H_2O$ | 53 g |
| Distilled water | 1000 mL |
| Magnesium sulfate | |
| $MgSO_4 \cdot 7H_2O$ | 300 g |
| Distilled water | 1000 mL |
| Ammonium nitrate | |
| $NH_4NO_3$ | 450 g |
| Distilled water | 1000 mL |
| Potassium phosphate monobasic | |
| $KH_2PO_4 \cdot 7H_2O$ | 200 g |
| Distilled water | 1000 mL |
| Potassium phosphate dibasic | |
| $K_2HPO_4 \cdot 7H_2O$ | 200 g |
| Distilled water | 1000 mL |

Sanger and Granick medium preparation: 1 mL of trace elements solution, 1 mL of sodium citrate solution, 1 mL of iron chloride solution, 1 mL of calcium chloride solution, 1 mL of magnesium sulfate solution, 1 mL of ammonium nitrate solution, 0.55 mL of potassium phosphate dibasic solution and 0.5 mL of potassium phosphate monobasic solution was mixed together.

The constituents of medium deficient in iron are provided in Table 5.

TABLE 5

| Ingredient | Amount |
| --- | --- |
| Yeast extract | 1.00 g |
| Beef extract | 1.00 g |
| Tryptose | 2.00 g |
| Glucose | 10.00 g |
| Distilled water | 1000 mL |
| pH | 7.0 |

The constituents of a medium deficient in nitrogen are provided in Table 6.

TABLE 6

| Ingredient | Amount |
| --- | --- |
| Yeast extract | 1.00 g |
| Beef extract | 1.00 g |
| $FeSO_4$ | Trace amounts |
| Glucose | 10.00 g |
| Distilled water | 1000 mL |
| pH | 7.0 |

Modified media deficient in iron and nitrogen constituents are given in Table 7.

TABLE 7

| Ingredient | Amount |
| --- | --- |
| Yeast extract | 1.00 g |
| Beef extract | 1.00 g |
| Glucose | 10.00 g |
| Distilled water | 1000 mL |
| pH | 7.0 |

Sub-culturing of *Chlamydomonas reinhardtii*: Sub-culturing of *Chlamydomonas reinhardtii* was carried out in all the four different media namely nutrient broth medium, TAP medium, Sueoka's high salt medium and Sanger and Granik medium. Table 8 shows the microbial biomass on day 5 of growth in various growth media.

TABLE 8

| Microbial biomass growth in four different media | |
| --- | --- |
| Media | Biomass on $5^{th}$ day (g/L) |
| Nutrient broth | 15.8 |
| Sueoka's high salt medium | 13.2 |
| TAP media | 12.1 |
| Sanger and Granik | 10.9 |

It was identified that maximal biomass growth was observed in nutrient broth medium i.e. 15.8 g/L on the $5^{th}$ day and was used for further experiments. Microbial biomass growth is also possible in other media types different from those tested as described herein.

FIG. 1 shows the growth curve of the microbial biomass grown in the nutrient broth medium. It can be inferred that maximal biomass is achieved by 5-7 days of continuous culturing.

Figure 2:
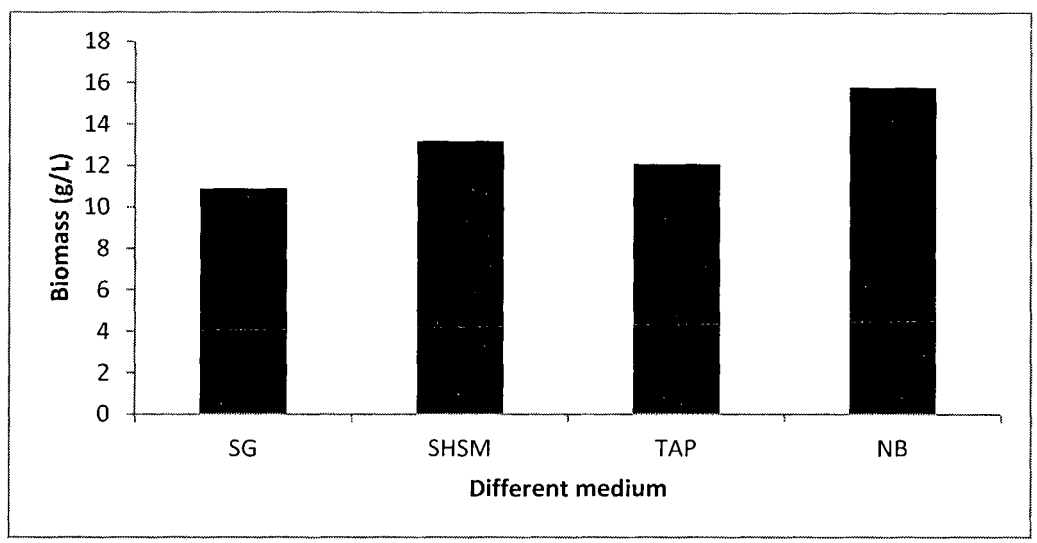
FIG. 2 shows a graphical representation of microbial biomass cultured in various growth media, in accordance with an embodiment of the present disclosure.

FIG. 2 is a graphical representation of the microbial biomass by day 5 when grown in various growth media. Highest microbial biomass was obtained from a culture grown in nutrient broth media compared to the other media tested. Hence, nutrient broth media was chosen for subsequent experiments.

Cultures were grown at 180 RPM on shakers under 24 hour light cycle. Growth was monitored daily over a period of 7 days by taking OD at 750 nm and weighing the dry biomass. Dry biomass was obtained by centrifuging the microbial culture at 1800 rpm for 10 minutes. The pellet was dried in a hot air oven at 60° C. for five minutes. Table 9 represents the increase in microbial biomass over a period of seven days of culturing in nutrient broth.

TABLE 9

| Day | Biomass (g\L) | OD at 750 nm |
| --- | --- | --- |
| 0 | 0.80 | 0.02 |
| 1 | 1.85 | 0.06 |
| 2 | 5.02 | 0.12 |
| 3 | 10.23 | 0.16 |
| 4 | 13.56 | 1.11 |
| 5 | 15.80 | 1.56 |
| 6 | 16.42 | 1.64 |
| 7 | 16.73 | 1.64 |

Example 2

Effect of Glucose Concentration and Light Cycle on Microbial Biomass

A preliminary study was conducted using varying concentrations of glucose and light cycle period as parameters for maximizing microbial biomass. Table 10 shows the effect of various concentrations of glucose or light cycle period on microbial biomass yield after five-days.

TABLE 10

| Run | Factor 1: Glucose concentration (g\L) | Factor 2: Light cycle (hours) | Biomass (g\L) |
|---|---|---|---|
| 1 | 12.50 | 4.69 | 27.9 |
| 2 | 12.50 | 24.00 | 9.46 |
| 3 | 1.89 | 16.00 | 13.2 |
| 4 | 20.00 | 24.00 | 21.26 |
| 5 | 20.00 | 8.00 | 54 |
| 6 | 23.11 | 16.00 | 58 |
| 7 | 5.00 | 24.00 | 11.1 |
| 8 | 5.00 | 8.00 | 30 |

It can be inferred from Table 10 that varying the concentration of glucose in the growth media significantly affects the microbial biomass yield. Similarly, variations in light cycle period also significantly affect the microbial biomass yield. The results also reveal that at a particular combination of glucose ranging from 20.0 g/L-24.0 g/L of glucose and 8-hours-16-hours of light cycle period gives maximal microbial biomass concentration. The biomass yield results denoted in Table 10 is representative of multiple independent experiments carried out.

Example 3

Enhanced Lipid Production in Microbial Cells Cultured in Modified Medium

After microbial growth in unmodified nutrient broth growth media, the cell suspension was centrifuged at 1008RCF for five-minutes. The pellet was washed with sterile distilled water once and weighed in a laminar flow hood. The weight was 1.673 g/100 mL of nutrient broth. The pellet was subsequently transferred to a modified growth media deficient in iron (Table 5) or nitrogen (Table 6) or both iron and nitrogen (Table 7) and assayed for lipid presence and TAGs was quantified.

Figure 3:
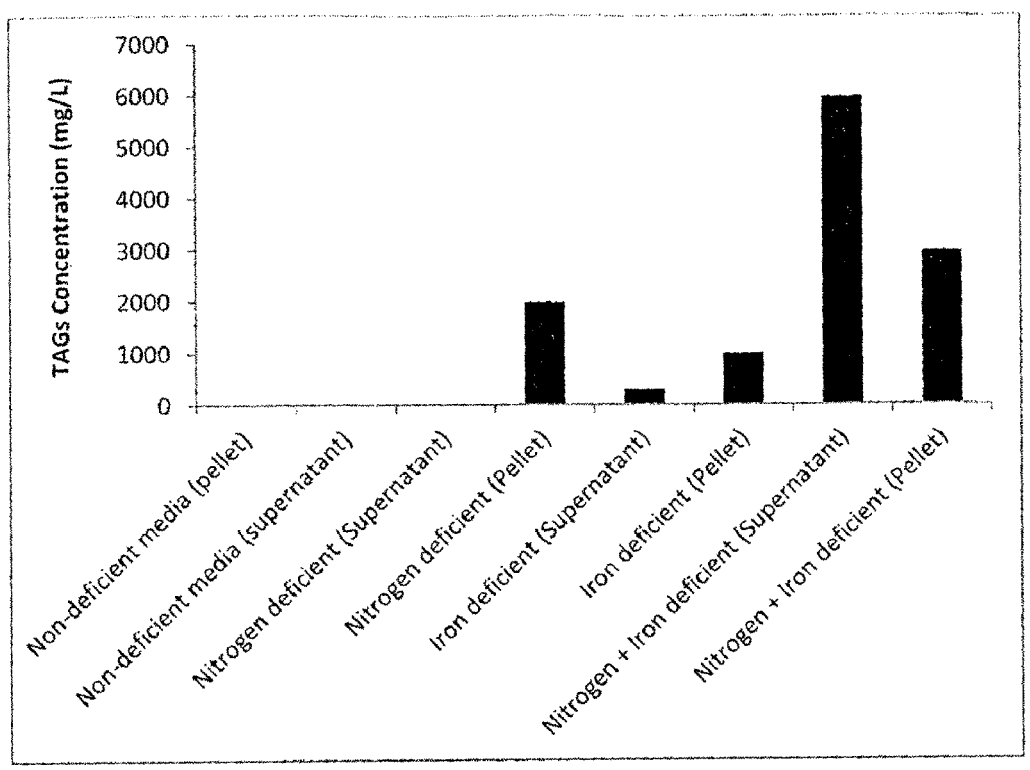
FIG. 3 shows a graphical representation of the quantification of intra-cellular and extra-cellular TAGs concentration and total amount in microbial cultures grown in various nutrient conditions, in accordance with an embodiment of the present disclosure.

It can be inferred from FIG. 3 that there is no TAGs production in microbial cells when grown in unmodified media. When microbial cells are grown in a modified media deficient in nitrogen alone, TAGs production is induced in contrast to microbial cells grown in unmodified media. TAGs produced in microbial cells grown in nitrogen deficient media accumulate intra-cellularly. Microbial cells grown in a modified media deficient in iron alone also results in TAGs production, and 25% of the TAGs are secreted extra-cellularly. Surprisingly, when a microbial culture is grown in a modified medium deficient in both nitrogen and iron, there is enhanced TAGs production by the microbial cells. There is also an enhanced TAGs secretion by the microbial cells into the extra-cellular milieu. 66% of TAGs produced by the microbial cells are secreted extra-cellularly. Table 11 shows the concentration and amount of TAGs produced by the microbial culture (100 mL) when grown in various deficient media.

TABLE 11

| Media type | TAGs concentration | TAGs amount (100 mL culture) |
|---|---|---|
| Unmodified media (pellet) | 0 mg/L | 0 mg |
| Unmodified media (supernatant) | 0 mg/L | 0 mg |
| Iron deficient (pellet) | 1000 mg/L | 100 mg |
| Iron deficient (supernatant) | 300 mg/L | 30 mg |
| Nitrogen deficient (pellet) | 2000 mg/L | 200 mg |
| Nitrogen deficient (supernatant) | 0 mg/L | 0 mg |
| Iron + Nitrogen deficient (pellet) | 3000 mg/L | 300 mg |
| Iron + Nitrogen deficient (supernatant) | 6000 mg/L | 600 mg |

While TAGs synthesis and extra-cellular secretion was tested on modified media as defined in Table 5, 6 or 7, TAGs production, and extra-cellular secretion can also be induced in other media compositions deficient in iron and nitrogen.

The following tests were carried out to detect presence of lipids in the extra-cellular milieu.

Solubility test: Solubility test is based on the property of solubility of lipids in organic solvents and insolubility in water. The principle of solubility test is based on the fact that due to lesser specific gravity of oil, it will float on water. 3 ml of organic solvent was taken in each test tube and five drops of sample was added in all the tubes. It was observed that the sample dissolved in organic solvents i.e. chloroform and ether, however it was insoluble in water and ethanol. It was concluded that the given sample is a lipid.

Saponification test: 2 mL of the supernatant was added to 5 mL of alcoholic KOH and vortexed briefly for five-minutes. The vortexed sample was placed in boiling water bath for 15 minutes. Table 12 shows the results of saponification test results. It was observed that there was formation of foam on shaking of the test tubes.

TABLE 12

| Media | Days | Supernatant - Foam | Pellet - Foam |
|---|---|---|---|
| Nitrogen deficient media | 1 | − | + |
| | 2 | − | + |
| | 3 | − | + |
| | 4 | − | ++ |
| | 5 | − | +++ |
| Iron deficient media | 1 | − | − |
| | 2 | − | + |
| | 3 | − | + |
| | 4 | + | + |
| | 5 | ++ | + |
| Nitrogen and iron deficient media | 1 | − | + |
| | 2 | + | + |
| | 3 | ++ | + |
| | 4 | +++ | + |
| | 5 | ++++ | + |

The following tests were carried out to detect or quantify TAGs specifically in the extra-cellular milieu.

Acroleintest: Acrolein (propenal) is the simplest unsaturated aldehyde. It is a colorless liquid with a piercing, disagreeable, acrid smell. The smell of burnt fat (as when cooking oil is heated to its smoke point) is caused by glycerol in the burning fat breaking down into acrolein. It is produced industrially from propylene and mainly used as a biocide and a building block to other chemical compounds, such as the amino acid methionine.

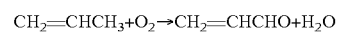

$$CH_2=CHCH_3+O_2 \rightarrow CH_2=CHCHO+H_2O$$

Acrolein is prepared industrially by oxidation of propene. The process uses air as the source of oxygen and requires metal oxides as heterogeneous catalysts. 5 mL of supernatant was taken to which 0.1 g of solid potassium bisulphate was added and heated over Bunsen burner.

Quantification of TAGs by isopropanol method: Working standard solution was prepared by mixing 3 mL stock (Tripalmitin) with 10 mL isopropanol. Different volumes (blank, 0.2, 0.4, 0.6, 0.8, 1.0 ml.) of working standard solutions were added in each tube. 1 mL of test solution (both supernatant and pellet for all the media) is taken in a separate test tube. The pellet was grounded in a pestle and mortar and lipids were extracted with choloroform. Isopropanol solution is added in each test tube so as to make it upto 2 mL. In each test tube, 0.6 mL of saponification reagent, 1 mL of sodium meta per iodate, 0.5 mL of acetyl acetone is added. Each test tube was shaken and kept in boiling water bath for 30 minutes. It was cooled and absorbance was measured at 405 nm.

The amount of triglycerides produced by the microbial culture grown in a modified media deficient in iron and nitrogen is 6 gTAGs/L when grown in presence of glucose concentration of 20 g/L, which is equivalent to 75% conversion of carbon to TAGs.

We claim:

1. A process of enhanced production and extra-cellular secretion of lipids comprising:
   a. obtaining a biomass of a microalgae, wherein the microalgae are selected from the group consisting of *Chlamydomonas reinhardtii, Chlamydomonas caudate Willie, Chlamydonomas moewusii, Chlamydonomas nivalis*, and *Chlamydonomas ovoidae*; and
   b. culturing the biomass of said microalgae in a modified growth medium deficient in nitrogen and iron, wherein the modified growth medium deficient in nitrogen and iron comprises:
      i) yeast extract in the range of 0.05%-0.2% (w/v);
      ii) beef extract in the range of 0.05%-0.2% (w/v); and
      iii) glucose in the range of 0.5%-3.0% (w/v), wherein the production and extra-cellular secretion of lipids by the microalgae biomass cultured in said modified growth medium deficient in nitrogen and iron is enhanced.

2. The process as claimed in claim 1, wherein the modified growth medium deficient in nitrogen and iron comprises:
   a. 0.1% (w/v) yeast extract;
   b. 0.1% (w/v) beef extract; and
   c. 2.3% (w/v) glucose.

3. The process as claimed in claim 1, wherein the pH of the modified growth medium deficient in nitrogen and iron is in the range of 6.5-7.5.

4. The process as claimed in claim 1, wherein the biomass of the microalgae is cultured in said modified growth medium deficient in nitrogen and iron subjected to a light cycle period ranging from 4.69-hours to 24-hours.

5. The process as claimed in claim 4, wherein the biomass of the microalgae is cultured in said modified growth medium deficient in nitrogen and iron subjected to a light cycle period ranging from 12-hours to 18-hours.

6. The process as claimed in claim 1, wherein 50%-70% (w/v) of lipids produced is secreted extra-cellularly.

7. The process as claimed in claim 1, wherein more than 90% (w/v) of the extra-cellularly secreted lipids are triglycerides.

* * * * *